(12) United States Patent
Dixon et al.

(10) Patent No.: US 8,944,008 B2
(45) Date of Patent: Feb. 3, 2015

(54) FORCE MEASUREMENT

(75) Inventors: Michael John Dixon, Ely (GB); Polly Margaret Taylor, Ely (GB); Benjamin Dixon, Ely (GB)

(73) Assignee: Topcat Metrology Limited, Ely, Cambridgeshire (GB)

( * ) Notice: Subject to any disclaimer, the term of this patent is extended or adjusted under 35 U.S.C. 154(b) by 184 days.

(21) Appl. No.: 13/440,310

(22) Filed: Apr. 5, 2012

(65) Prior Publication Data

US 2012/0255500 A1 Oct. 11, 2012

(30) Foreign Application Priority Data

Apr. 8, 2011 (GB) .................................. 1105990.4

(51) Int. Cl.
| | |
|---|---|
| *A01K 1/03* | (2006.01) |
| *G01L 1/14* | (2006.01) |
| *A61B 5/00* | (2006.01) |

(52) U.S. Cl.
CPC ................ *G01L 1/142* (2013.01); *A61B 5/4827* (2013.01); *A61B 2503/40* (2013.01); *A61B 2503/42* (2013.01)
USPC ........... 119/421; 73/866.5; 600/557; 600/587

(58) Field of Classification Search
CPC ............ A61B 5/03; A61B 5/11; A61B 19/00; A61B 39/04; G01L 5/00; G01L 1/04; G01D 21/00
USPC ............. 119/421; 600/557, 587, 592; 73/760, 73/866.5, 862.08, 862.321, 862.326
See application file for complete search history.

(56) References Cited

U.S. PATENT DOCUMENTS 1,245,130 A * 10/1917 Somers .......................... 33/32.2
3,260,236 A 7/1966 Jones
(Continued)

FOREIGN PATENT DOCUMENTS

| DE | 2333502 | 7/1973 |
|---|---|---|
| DE | 4336267 | 10/1993 |

(Continued)

OTHER PUBLICATIONS

GB Search Report for corresponding patent application No. GB1105990.4 dated Aug. 9, 2011.
(Continued)

*Primary Examiner* — Rob Swiatek
*Assistant Examiner* — Ebony Evans
(74) *Attorney, Agent, or Firm* — Renner, Otto, Boisselle & Sklar, LLP

(57) ABSTRACT

A rodent enclosure dimensioned in length, width and height so as to allow a rodent to run freely along the length of the enclosure, but not turn around without standing on its hind legs. The enclosure has a floor with bars extending transversely to allow access for a force sensor's probe from below. A force measurement device for use with the rodent enclosure to measure the tactile response of a rodent comprising a measurement probe connected to a device body. The probe has a tip which can be engaged with a rodent's paw through the floor of the enclosure. The device body has a fixed body part and a rotatable body part arranged to allow relative rotation between them. A rotation sensor detects the relative rotation and outputs a measurement parameter having values that are calibrated against force values associated with forces applied to the probe's tip.

9 Claims, 7 Drawing Sheets

(56) References Cited

U.S. PATENT DOCUMENTS

| | | | | |
|---|---|---|---|---|
| 3,550,431 | A | * | 12/1970 | Cotta et al. .......................... 73/37 |
| 3,857,364 | A | | 12/1974 | Miller, Jr. |
| 4,313,446 | A | * | 2/1982 | Kanatani ....................... 600/557 |
| 5,469,862 | A | | 11/1995 | Kovacevic |
| 5,823,969 | A | * | 10/1998 | Christy ........................ 600/557 |
| 6,234,976 | B1 | * | 5/2001 | Linden ......................... 600/557 |
| 2013/0174675 | A1 | * | 7/2013 | Chen ........................... 73/866.5 |

FOREIGN PATENT DOCUMENTS

| | | |
|---|---|---|
| EP | 0369570 | 7/1989 |
| GB | 2465157 | 5/2010 |
| SU | 1110449 A1 | 8/1984 |
| WO | 2005/084147 | 9/2005 |
| WO | 2010/024492 | 3/2010 |
| WO | 2010/024843 | 3/2010 |

OTHER PUBLICATIONS

"Von Frey Testing is Just Plain Difficult", Topcat Metrology, 2011, retrieved Aug 8, 2011: http://wwwl11ousel11eLco.uk/about-the-topcatelectronic-von-frey/.

"MouseMet from Topcat Metrology", Topcat Metrology, 2011, retrieved 8 Aug 8, 2011: http://www.electronicvonfrey.co.uk/.

Electronic von Frey, Sornedic, http://wwwsomedicse/article.php718.

"A Feedback-Controlled Dynamic Linear Actuator to Test Foot Withdrawal Thresholds in Rat," Bove et al., J Neurosci Methods, Jun. 15, 2007; 163(1): 44 51, retrieved Aug 8, 2011: http://www.ncbinlmnih.gov/pmc/articles/PMC2002475/pdf/nihl11s-23904.pdf.

* cited by examiner

FORCE MEASUREMENT

This application claims priority to Great Britain Application No. 1105990 4 filed Apr. 8, 2011, which is hereby incorporated by reference.

BACKGROUND OF THE INVENTION

The invention relates to a force measurement of the sensitivity threshold of animals or humans, and in particular the sensitivity or nociceptive (pain) threshold of rats and mice as is needed for medical research, such as to measure analgesic effects.

The measurement of mechanical sensitivity, or nociceptive (pain) threshold has long been used in many areas of medical research, in particular as a measure of analgesic effect. The hypothesis is that, after a force (or pressure) threshold figure has been established without treatment, the administration of an analgesic will elevate that threshold.

In humans, and in larger animal species, so called mechanical algometers, palpometers, dolorimeters or aesthesiometers are used. These are essentially hand-held force gauges, with a tip of suitable cross-sectional area and profile for the species and test site. The tip is pushed with a progressively increasing force into the surface tissue of the subject until a response is elicited. This is assumed to be the nociceptive threshold. The response may be vocal or behavioral. Ethics demand that the stimulus is removed rapidly at the threshold.

Such methods become difficult to implement at low forces, as are required for small animals such as rats and mice. The force transducer becomes unwieldy compared to the size of the animal and, if the force is applied by hand, overly sensitive to the inevitable slight hand tremor of the operator.

Historically, "von Frey filaments" have been used to overcome these problems in small animals [1, 2]. Von Frey filaments are sold by Ugo Basile for example [3]. Von Frey filaments are thin filaments of a flexible material with a high elastic strain range, supplied as a set of differing diameters but of the same length. As the diameter increases, so does the compressive force required for buckling. The diameters of the filaments are arranged so that, when a compressive force is applied along their axis, the buckling forces are in useful increments of the total force range to be investigated. The range of von Frey filaments or "hairs" typically runs from 0.008 g to 300 g. The highest diameter is about 1.3 mm and the lowest less than 0.1 mm. (In practice, presumably because of manufacturing restrictions, these force increments are very un-equal.) Thus the successive application of progressively thicker filaments to the test site on the subject will provide a force which increases in a number of un-equal steps.

Typically, for the measurement of mechanical thresholds on rats and mice, the ventral surface of the paw is used for testing, with the animal allowed to move in 2 axes in a cage whose base is formed of an open grid. Von Frey filaments are advanced upwards towards the pad of the paw by the tester, through the grid. Typically, the behavioral response is for the animal to lift its foot.

Considerable judgment is required by the tester as, at some point during the successive application of a series of von Frey filaments of progressively increasing diameter, the force will become sufficient to simply lift the foot, rather than the animal withdrawing it voluntarily. This is not a valid test.

In summary, von Frey filaments have a number of drawbacks:

1. The test site is subjected to a sequence of tests before a result is reached. If the subject reacts to the first filament, then only one test is made and the result is limited to having established that the threshold force is the force associated with the first filament or less. If reaction occurs later during a second or further test, the result is still only within a band of forces defined by the buckling force separation between adjacent filament sizes used in the test. This is time consuming and undoubtedly has implications for a behavioral response. Previous stimuli may also change the perception of subsequent ones.

2. As the filaments are, of necessity, of different diameters (in order to achieve a progressively increasing force), the area of tissue on which they act also changes (each filament is cleaved across its end to achieve a nominally flat disc of contact). As the area of tissue changes so does the pressure beneath the surface (pressure=force/area), and potentially also the number of nociceptors that are triggered by the stimulus.

3. The buckling load for each filament, while repeatable when the filament is new and undamaged, reduces substantially as soon as the filament takes a set or curve, through use, misuse or damage.

4. The contact area changes as the filament buckles, from a flat disc to a curved line edge contact. This changes the feel of the filament at the threshold and may have implications for the animal's response to the next test.

5. The use of a number of successive tests requires the test subject to remain stationary. Healthy rats and mice are generally disinclined to do this. The experimenter, viewing a square or rectangular cage from the side, must therefore follow the rodent while attempting to push the filaments through the gaps in the grid without touching the grid (the friction from which would invalidate the test).

6. Since the transducing element is stiff up to the point at which it buckles, hand tremor from the operator is transmitted as a variation in force during the force ramp, although the maximum force cannot exceed the rated force for that filament.

There have been, in recent years, a number of attempts to produce alternatives to the traditional von Frey systems, for example:

Electronic von Frey Anethesiometer, model 2390
IITC Inc Life Science
23924 Victory Blvd
Woodland Hills
Calif. 91367
Electronic von Frey, model BSEVF3
Harvard Apparatus
Fircroft Way
Edenbridge
Kent
TN8 6HE
United Kingdom
37450 Dynamic Plantar Aesthesiometer [4]
Ugo Basile North America Inc
414 West Main Street
Collegeville
Pa. 19426
Electronic Von Frey Sensebox [5]
Somedic AB
Box 194
SE-242 22 Horby
Sweden These solutions are, in one form or another, low capacity force gauges with a single thin probe to apply the force. These systems are generally difficult to use, for two reasons:

Firstly, the force producing and sensing mechanism is influenced greatly by any hand tremor of the operator. This is because the system is fundamentally much stiffer than a von Frey filament over the entire measurement range: any small movement results in a relatively large change of force. This may be seen by attempting to push down with a small but constant force on a set of digital kitchen scales (where the deflection of the force transducer within will be millimeters or fractions of millimeters for the entire force range); the reading will be seen to fluctuate considerably due to hand tremor. A von Frey filament, in contrast, is only stiff up to the point at which it buckles; at that point it becomes a very soft spring where the force applied is relatively insensitive to hand tremor.

Secondly, for laboratory animals, the time window available for a test is small (perhaps 3-5 seconds) before the animal moves to a different location within the cage. Some of the systems available require the operator to follow a force/time ramp on a computer screen while applying the force. This is impractical while looking at the mouse's foot and unrealistic in the time frame available.

Attempts have also been made to automate the force application process by means of a motor driven probe which advances up through the grid to the foot from a movable platform. This platform must still be manually positioned relative to the foot in X and Y by the operator (using a mirror), and requires the animal to remain motionless for the time of the test (5 seconds or more).

The problems outlined above apply to both rats and mice. They are however greater for mice, due to their smaller size and correspondingly lower threshold force. As an example, mechanical thresholds for mice are in the order of 1-4 grams force, and up to 50 grams force or more for rats. As laboratory mice make up 90% of the animal laboratory rodent population, and therefore a similar proportion of all nociceptive testing, there is scope for improvement of the current approaches.

SUMMARY OF INVENTION

The invention has a number of different aspects including: a force measurement device, a computer program product, a data acquisition system, a rodent enclosure, various kits of two or more of the above, and a method of making a force measurement on a rodent.

In one aspect, the invention provides a force measurement device, comprising: a fixed body part and a rotatable body part mutually arranged to allow relative rotation between them about a common rotational axis; a resilient biasing member mounted at one end to the fixed body part and at the other end to a rotatable transducer part which is rotatable independently of, and relative to, the rotatable body part; a probe having a tip portion extending generally tangentially to the rotational axis and terminating at one end in a tip and at the other end in a junction with an arm portion extending generally radially to the rotational axis and connecting at its other end to the rotatable transducer part so that angular displacement of the fixed part relative to the arm portion stores or releases energy in the resilient biasing member and also causes rotation of the transducer part relative to the fixed body part; and a rotation sensor operable to detect the amount of angular displacement between the transducer part and the fixed body part, and to output a measurement parameter having values that are calibrated against force values associated with forces applied to the probe's tip.

The device can be implemented as a hand-held unit if the fixed body part and the rotatable body part each have a handle portion to allow the device to be held in each hand by an operator.

With this design, a device can be provided for the application and measurement of forces up to 5 grams force via a soft spring (i.e. one of high compliance), thereby requiring a large displacement from the operator to apply a small force and thus minimizing the effects of hand tremor on said forces. In such a device, application of the force to the soft spring is achieved by rotation or twisting, thereby making it easy to apply by hand in a vertical direction (Z) while maintaining control and position of the probe in the horizontal (X and Y) planes. A device can thus be realized which allows the force to be easily and repeatably applied by an operator who is sitting comfortably with their forearms suitably supported over a suitable time period, typically 3-5, or perhaps up to 10 seconds, a few seconds being the longest amount of time which a healthy mouse can realistically be expected to keep still.

Hand tremor by the operator during the application of the force is moderated by the use of such a "soft" force transducer; i.e. one which requires a large displacement to achieve a small force. This may be visualized using the example of the kitchen scales above; if one were to press down via a soft coil spring (one with a low rate so that a small force causes a relatively large change in length) then the displacements of the hand due to tremor would cause only small changes in the force transmitted by the spring.

In an embodiment of the invention, the rotatable transducer part comprises a rotatable sensor element which is arranged facing a fixed sensor element attached to the fixed body part, wherein relative rotation of the rotatable and fixed sensor elements causes variation in the value of the measurement parameter. The measurement parameter can be electrical or optical, for example. In one embodiment, the rotatable and fixed sensor elements can be made of plates with electrically conductive portions patterned so that their area of mutual overlap, as viewed in the direction of their common rotational axis, varies with the amount of their relative rotation, the measurement parameter being capacitance between the plates. Preferably, the area of mutual overlap when no energy is stored in the resilient biasing element is at least 10% of the maximum mutual overlap.

In another aspect, the invention provides a computer program product bearing machine executable instructions for processing force measurement data comprising: an input part operable to receive sets of force measurement data collected by a force measurement device, each data set being a measurement of force as a function of time; a display part operable to present a graphical user interface to an operator including (i) a graph showing force as a function of time extracted from the force measurement data set (ii) a visual representation of a range of acceptable evolutions of force as a function of time overlaid on the graph, and (iii) an input via which the operator is prompted to provide an input decision accepting or rejecting the force measurement data set based on the operator's visual inspection of the graphical user interface; and an output part operable to output those force measurement data sets that have been accepted by the operator as validated force measurement data sets.

The fact that the output data sets are of validated data may be implicit if the computer program is configured only to output validated data sets. Alternatively, the validity of the output data sets may be explicit if the computer program is configured to output validated data sets with a validation flag. In this latter case, the computer program could if desired also output invalidated data sets as well with the invalidated data sets having their validation flag set to indicate they had been (provisionally) rejected.

Each force measurement data set is preferably time stamped with the time of acquisition and optionally also with other data specific to the data set.

In another aspect, the invention provides a data acquisition system comprising: a computer loaded with the computer program product above; and an interface arranged to receive force data from a force measurement device. Advantageously the system further comprises a user input device operable to receive operator commands and connectable to the computer to communicate the operator commands as command data to the computer program. The command data preferably includes a command to indicate a provisional decision by the operator on validity or invalidity of the force measurement data set just acquired and/or a command to indicate completion of acquisition of a force measurement data set. A single command may be used to communicate both completion of acquisition, and provisional validity, of a data set. Each force measurement data set is preferably time stamped with a time taken from the time of the command data. A system for measurement and recording can thus be provided which allows for post-test selection of valid tests against a number of criteria.

In another aspect, the invention provides a rodent enclosure having at least a floor, two side walls and two end walls, and optionally also a roof. The enclosure is dimensioned in length, width and height so as to form a run for a rodent of pre-specified size and type along the length of the enclosure between its ends. The width is dimensioned to allow the rodent to run freely along the length of the enclosure. The width is limited, at least away from the ends of the enclosure, so that the rodent cannot turn around while standing on all fours, but can turn around when standing on its hind legs. The enclosure has a floor with apertures along its length and width to allow access for a force sensor's probe filament from below to the rodent's paw pads. Optionally, one or both ends of the enclosure have a widened part where the rodent can turn around while standing on all fours. It is therefore possible to provide an enclosure for a mouse, rat or other rodent which provides for stress-free and natural behavior but which, by its proportions, encourages movement in only one plane. Usually a roof will be needed to retain the subject unless the walls are made sufficiently high, or otherwise configured, to prevent escape.

While this enclosure design is especially useful for the currently disclosed force measurement device, it may also be used when measuring with known force sensors, and provides significant advantages over known rodent enclosures which allow the animal to move across the floor area in all directions, i.e. the rodent is free to run around in circles or any desired direction. This greater freedom of movement (two-dimensional instead of one dimensional) makes it more difficult to obtain a valid force reading with a prior art enclosure of this kind.

In one embodiment, the floor is provided by bars extending across the enclosure, the bars being spaced apart sufficiently to allow probe filament access to the rodent's paw pads. Alternatively a square mesh or other two-dimensional mesh could be used to form the floor where the mesh apertures are dimensioned to be sufficiently large to allow probe filament access. The apertures are preferably as large as possible to maximize the area of the rodent's paw pad that is available for contact with the probe tip along the length dimension of the enclosure while sufficiently small so as not to prevent the rodent's ability to run lengthwise along the floor.

The bars or mesh is preferably dimensioned in cross-section to allow a rodent's paws to grip the bars with the toes of the paw. For a mouse, and assuming circular cross-section bars, suitable diameters are likely to lie in the range 0.5 to 3 mm. For a rat, and assuming circular cross-section bars, suitable diameters are likely to lie in the range 1 to 5 mm.

The lengthwise separation between adjacent bars or mesh cells is preferably greater than, or at least one of 50, 60, 70, 80 or 90% of, the length of the rodent's back paw to provide a conveniently large area of paw available for testing. The lengthwise separation is further preferably not too much larger than the length of the rodent's back paw, since too large a separation will tend to inhibit the rodent's natural behavior. Specifically, the lengthwise separation is preferably no more than 110, 120, 130, 140, 150, 200, 250 or 300% of the length of the rodent's back paw. The specific ranges of lengthwise separation envisaged may therefore be between any one of these specified minimum separations and any one of these specified maximum separations, e.g. between 0.5 to 3 times the length of the rodent's back paw, 1 to 2 times etc.

For a mouse run, spacing of the bars (assuming the length of a mouse's foot to be 10 mm) will typically lie in the range of 5 mm to 20 mm or 30 mm, preferably 7 mm to 15 mm, still more preferably 8 mm to 12 mm, the bars being of a diameter between 0.5 mm and 3 mm. Preferably, the width of the run will probably lie in the range of 25 mm to 40 mm and the length between 100 mm and 200 mm.

For a rat run, spacing of the bars (assuming the length of a rat's foot to be 20 mm) will typically lie in the range of 10 mm to 40 mm or 60 mm, preferably 15 mm to 35 mm, still more preferably 20 mm to 30 mm, the bars being of a diameter between 1 mm and 5 mm. Preferably, the width of the run will probably lie in the range of 60 mm to 90 mm and the length between 300 mm and 500 mm.

The rodent enclosure preferably includes supports, e.g. legs, to elevate the floor of the enclosure above a base surface, e.g. a workbench, when the enclosure is placed on the base surface, thereby to provide probe filament access through the floor of the enclosure to an operator.

The rodent enclosure has side walls, end walls and/or a roof panel which are sufficiently see through to allow sight of a rodent in the enclosure by an operator. In particular, it is preferred that the walls are see through near the level of the floor, i.e. the lower parts of the walls, to permit ease of viewing of the rodent's feet by an operator with his or her eye level approximately level with, or slightly above, the floor plane where the rodent's feet are situated. The sufficiently see-through walls and/or panels can be tinted so as to be see-through for an operator, but opaque to the type of rodent the enclosure is designed for. Specifically, a colored tint can be used known to be opaque for the strain of mouse being tested, in order to prevent the rodent from seeing the operator while leaving the rodent visible to the operator.

Further aspects of the invention relate to a kit comprising combinations of the elements described above, or an assembly of parts for each such element, such as two or more of: a force measurement device, or an assembly of parts therefor; a rodent enclosure, or an assembly of parts therefor, and a computer program product.

Another aspect of the invention is a method of making a force measurement of a rodent comprising:
 (a) providing an operator with a force measurement device as described above connected to a data acquisition system as described above;
 (b) placing the rodent in a rodent enclosure as described above to allow access for the force sensor's probe filament from below;
 (c) the operator placing the tip of the probe filament in contact with a paw pad of the rodent and then actuating the force measurement device by gradually increasing the amount of relative rotation between the fixed and rotatable body parts so as to increase gradually the force applied to the rodent's paw pad until such time as the rodent withdraws its paw as a result of a tactile response; and (d) the force measurement device supplying a force measurement data set to the computer via the interface, the data set being a measurement of force as a function of time as measured during step (c).

For rodent measurements, the probe tip is preferably sized to provide a tissue pressure that causes the rodent to lift its foot somewhere within the center part of a calibrated force range, so that subjects that are more or less sensitive than the norm (e.g. as a result of their treatment or state of health) have reactions that lie within the calibrated force range.

The probe tip may be flat or curved. A curved tip will reduce the possibility of high pressures being applied locally at the edges of the tip that are not representative of the tip area as a whole. In specific rodent test examples made to date, probe tips in the range 0.2 to 0.4 mm diameter have been used.

The method optionally further comprises the operator providing a command to the computer to indicate provisional validation or rejection of the data set acquired in step (c).

BRIEF DESCRIPTION OF THE DRAWINGS

For a better understanding of the invention and to show how the same may be carried into effect reference is now made by way of example to the accompanying drawings.

DETAILED DESCRIPTION

Figure 1A:
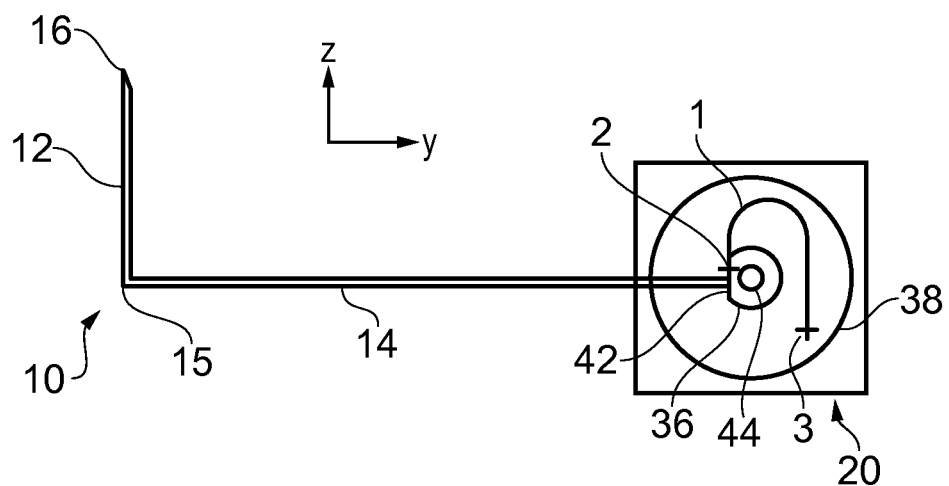
FIG. 1(a) is a schematic side section of a force measurement device in its rest or equilibrium position when its spring is not storing any significant amount of energy and with the arm of its measurement probe extending horizontally.
Figure 1B:
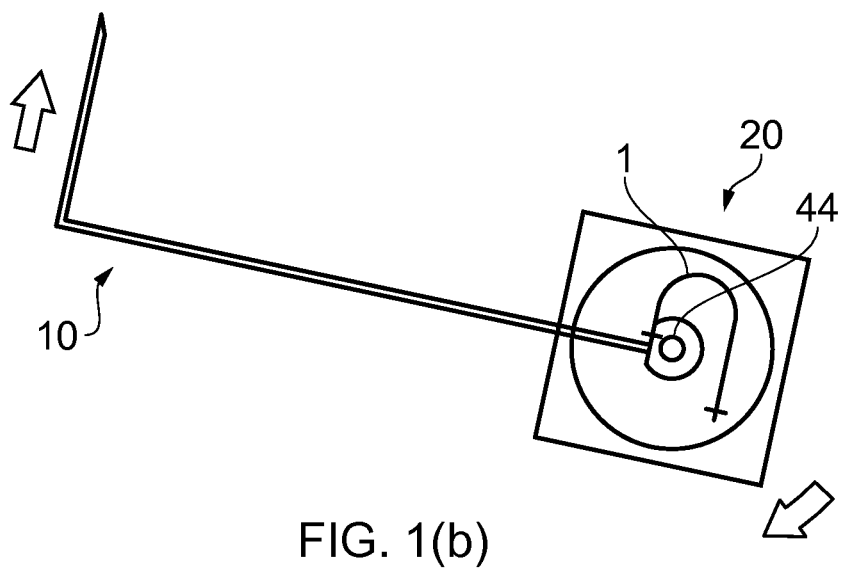
FIG. 1(b) corresponds to FIG. 1(a) but shows the force measurement device when it has been rotated by the operator in the absence of any resistance at the probe tip.
Figure 1C:
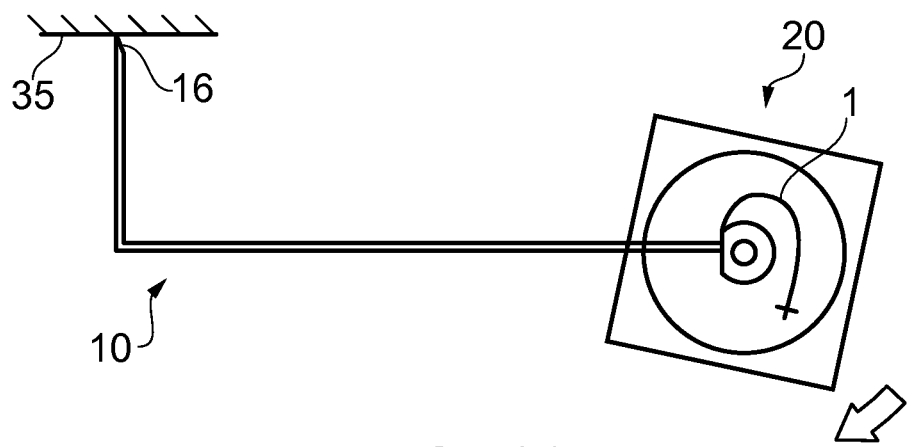
FIG. 1(c) corresponds to FIG. 1(a) but shows the force measurement device when its spring is energized as a result of relative rotation of its components when the probe tip is abutting an object.
Figure 2:
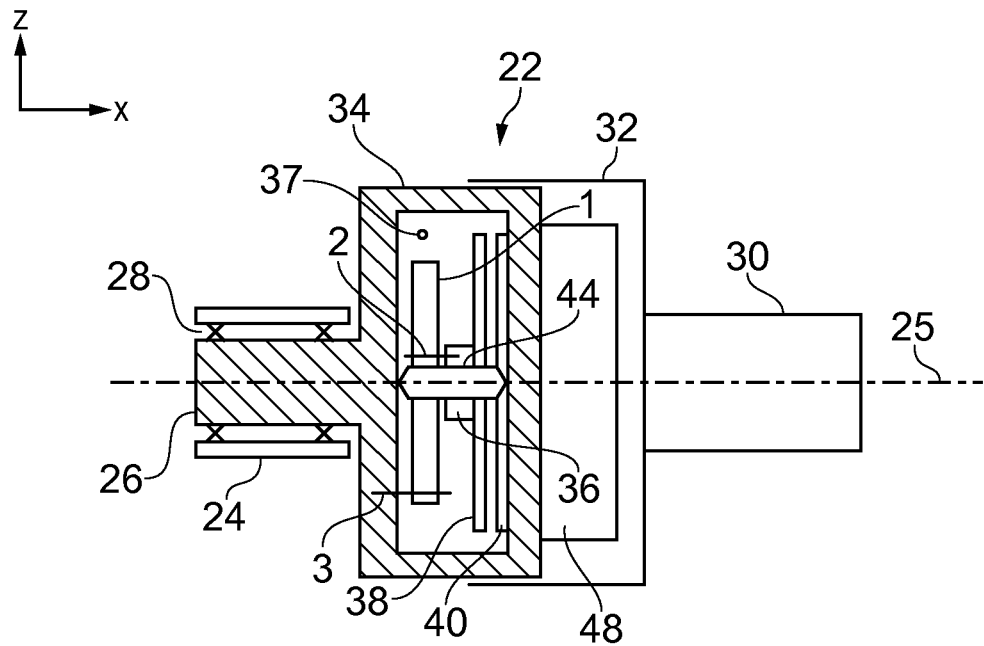
FIG. 2 is a schematic partial cross-section of the force measurement device of FIG. 1 from a side elevation 90 degrees rotated from FIG. 1.

A force measurement device is now described initially with reference to FIGS. 1(a), 1(b) and 1(c) and FIG. 2. FIGS. 1(a), 1(b) and 1(c) are schematic side sections views of the force measurement device in equilibrium and two non-equilibrium positions. FIG. 2 is a schematic partial cross-section of the same force measurement device from an end elevation rotated 90 degrees relative to FIG. 1.

Referring to FIG. 1(a), the force measurement device has a probe 10 comprising a tip portion 12 and an arm portion 14 which are joined at a junction elbow 15. The probe terminates in a tip 16 at the upper end of the tip portion 12. The tip of the probe is the contact area with the object to be sensed, which is the paw pad of a laboratory mouse in the present embodiment.

Other embodiments may be designed for arbitrary sensing objects which may include a wide variety of areas on the human or animal body, wherein animals can include laboratory rats, other rodents, other laboratory animals, and various types of pet animal. Inanimate objects may also be tested, for example robotic sensing parts. On the human body the contact areas could be points on the soles of the feet, including the toes.

The probe 10 is attached to the main body of the device, which is generally indicated with reference numeral 20.

Referring principally to FIG. 2, but also having regard to FIG. 1(a), the main body 20 can be subdivided into a fixed body part made up of several components, but generally indicated with reference numeral 22, and a rotatable body part in the form of a handle 24 rotatably mounted to an axle 26 of the fixed body part 22 by a roller bearing 28. The fixed body part 22 also includes a handle 30 which is joined to a first casing part 32 of the fixed body part 22. The first casing part 32 is fixed to a second casing part 34 which includes the axle 26 and also an interior chamber 37 which accommodates transducer parts of a rotation sensor as described further below. The handles 24 and 30 are thus able to rotate relative to each other about their common axis 25.

The end of the arm portion 14 is push fitted in a hole (not shown) extending into a collar 36 of a disc 38 perpendicularly to its chamfered face 42, wherein the collar 36 acts as a hub to mount the disc 38 on a spindle 44. The spindle, disc, collar and embedded end of the probe are all fixed together to co-rotate. The spindle 44 is journalled at either end on inner faces of a second casing part 34 of the device main body 22 as shown in FIG. 2.

The disc 38 forms a rotatable transducer plate facing a corresponding fixed disc 40 which is part of the fixed body part 22 by virtue of being mounted on an inner face of the interior 37 of the casing 34.

The pair of disc plates 38 and 40 form the transducer element of a rotation sensor capable of detecting the amount of angular displacement, and outputting a measurement parameter having values that are calibrated against force values associated with forces applied to the probe's tip. Rotation is sensed by the variation in capacitance between the two plates 38 & 40 which is converted to a voltage by an electronic module 48 housed in the interior of the casing part 32. This is done by measuring the change in current drawn by an oscillator circuit that has the variable capacitance as one element. An alternative implementation would be to use a bridge circuit with an AC carrier signal across it and to demodulate the output back to DC. The analogue voltage signal obtained from the varying capacitance of the capacitor is digitized by a suitable analogue-to-digital converter which may be integral with the electronic module 48, or may be part of the input/output (I/O) of a computer or other digital electronic processing unit to which the sensing device is connected.

Figure 3:
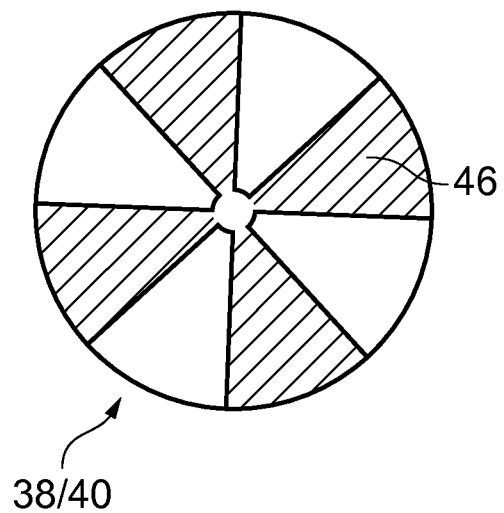
FIG. 3 is a plan view of a sensor plate of the force measurement device.

FIG. 3 is a schematic plan view of one of the sensor plates 38, 40. They both have the same design. Each plate 38/40 is made of an insulating material and has inserts or surface depositions of electrically conductive material in a rotationally symmetric pattern—four quadrants 46 in the illustrated example each spanning an angular range of 45 degrees or λ/4. Another number of pattern elements could be chosen, such as 2, 3, 5 or 6. The two plates 38, 40 are arranged such that, with the probe arm 14 in the horizontal position, i.e. rest position, the conductive areas 46 on the plates mutually overlap by a relatively small proportion of their areas, preferably at least approximately 5%, 10% or 15% of their area, and further preferably not by more than 20%, 30% or 40% of their area. A value of 10% is used in a specific example, where 10% overlap corresponds to an angular overlap of 45°/10=4.5° with a quadrant pattern. The initial overlap of the plates removes the non-linearity in the output from the sensor associated with the edge effects of capacitors. Rotation of the disc 38 from its rest position during application of a load therefore results in increased capacitance between the two plates as the degree of overlap increases. With a quadrant pattern having 4 fold rotational symmetry, the maximum angular travel for measurement is 45°, or $2\pi/2\times4=\pi/4$. If a pattern with n-fold rotational symmetry is used for the discs, then the angular measurement range is limited to a maximum of $2\pi/2n$ less whatever margin of initial overlap is provided in the rest position to suppress edge effects to an acceptable amount.

A hair spring 1 is connected at one end at location 2 to the disc collar 36 and at the other end at location 3 to an inner face of the interior chamber 37 of the casing 34. The disc 38 and spindle 44 thus rotate together independently of the fixed body part 22. When they do rotate relative to each other, this causes the hair spring 1 to be wound or unwound, storing or releasing energy therein, depending on the direction of the rotation, and also causes angular displacement of the rotating disc 38 relative to the fixed disc 40.

In use an operator holds the handles 24 and 30 with each hand, for example between thumb and forefinger, and actuates the device by rotating one handle relative to the other about their common axis of rotation 25

Referring to FIG. 1(*b*), if an operator rotates handle 30 in a clockwise direction as viewed along the +x axis, then, the probe will rotate the same way assuming the probe tip 16 is free. A rotation of this kind will not store any significant energy in the spring—only the small amount resulting from the change in load on the spring caused by the redistribution of the cantilevered probe's weight as it is lifted.

Referring to FIG. 1(*c*), if an operator rotates handle 30 in a clockwise direction as viewed along the +x axis when the probe tip 16 is abutting an object as illustrated by reaction surface 35, the probe 10 is prevented from moving. Instead, the rotation of the handle 30 is accommodated by tensioning of the spring 1 as shown by the transition from the rest position of FIG. 1(*a*) to the tensioned position of FIG. 1(*c*).

While horizontal and vertical have been used for simplicity in the above description, these labels imply that the device is to be used in a particular orientation. In fact, essentially the same design can be used in other orientations. For example, the device could be intended for use with the arm portion arranged to extend vertically and the tip portion horizontally. A more general definition of the relative directions of extent of the probe relative to the device's main body is thus as follows. The probe's tip portion 12 extends generally tangentially and perpendicularly to the rotational axis 25. The probe's arm portion 14 extends generally radially and perpendicularly to the rotational axis 25. One design consideration to be made when varying the intended orientation of the device is to vary the preload on the spring 1 to ensure the effects of the cantilevered weight of the probe in the rest position is cancelled out.

Accordingly, we have arranged a curved hair spring 1 (U shaped in the current design), attached radially at one end 2 to a disc 38 suspended on a spindle between low friction bearings and, at the other end 3, to an outer, fixed casing 34. An arm 14, protruding from the disc 38 and containing the probe tip 16 to contact the mouse's paw, is nominally horizontal, its weight being supported by preload in the spring. (It could also be counterbalanced by a mass on the other side of the disc 38). The disc 38 is thus balanced. In use, the operator holds the casing by two circular handles 24, 30 axial with the disc pivots. One handle 30 is fixed to the casing 32, while the other handle 24 rotates on bearings 28 supported on an axle 26 fixed to a casing part 34. In use the instrument is held between the thumb and forefinger of both hands, with the arm 14 pointing away from the operator and initially horizontal. The operator may then twist the casing by twisting the fixed handle with the right hand while supporting the handle with bearings with the left hand to keep the instrument horizontal. Such an action is easy for humans to perform without introducing displacements in other planes, particularly if the forearms are suitably supported. If the casing is twisted with nothing for the probe 10 to react against, as shown in FIG. 1(*b*), then the arm 14 and pointer 12 merely rotate upwards. If however, the probe pushes against the mouse's paw, as shown in FIG. 1(*c*), then the arm 14 remains horizontal and the disc 38 rotates relative to the casing 32, 34. A force is therefore applied to the arm 14 and probe tip 16 as the hair spring 1 bends.

With an example device, the "softness" of the spring is provided by a specification in which 45 degrees of rotation between the handles 24 and 30 are required when the probe tip 16 is abutting a reaction surface to achieve the full scale load of 4 grams force. The device is therefore relatively insensitive to hand tremor of a few millimetres, which result, at the end of an arm 14 which is 150 mm long, in a variation of only a few degrees in the rotation of the disc 38.

The action of twisting the handles 24 and 30 to apply the force is simple, intuitive and easy to accomplish controllably. Testers have, therefore, a good chance of applying the force to threshold before the mouse moves within the cage.

In summary, the embodiment above has described a handheld force measurement device, comprising: a probe having a tip portion extending generally vertically when in use and terminating in an upwardly facing tip and an arm portion extending generally horizontally in use and connecting at one end to the tip portion and at the other end to a mounting location; a fixed and a rotatable handle arranged to allow relative rotation between them when being held in each hand by an operator, wherein the probe is connected to the device at the mounting location where it is fixed to one end of a soft spring, the other end of the soft spring being connected so as to be rotationally fixed to the fixed handle, wherein a transducer part is arranged to have an angular position that follows angular motion of the probe's arm portion at the mounting location independently of the angular position of the fixed handle, so that increasing amounts of rotation of the handle 30 when the probe tip is abutting an object causes increasing amounts of loading of the soft spring, which transmits increasing amounts of force to the probe tip as well as causing a correspondingly increasing amount of relative rotation between the transducer part and the fixed handle; a rotation sensor operable to detect the amount of relative rotation between the transducer part and the fixed handle, and to output a measurement parameter having values that are calibrated against force values associated with forces applied to the probe tip. Additionally, the measurement parameter may be used to trigger a visual indicator, which may for example be conveniently mounted and visible on an external surface of the force measurement device, which operates when the force range of the measurement device is exceeded.

Other types of spring could be used, or more generally any suitable biasable resilient member. The embodiment uses a flat hair spring, namely a hair spring of rectangular cross section which is bent into a U shape. The cross-section of the spring could also be square, round, elliptical or other shape. Other geometries are also possible: a flat beam of any of the above cross-sections, a spring bent somewhere between a flat beam and a U section, or one bent beyond a U section to form partial or complete coils that lie within each other (like a conventional watch or clock hairspring). The spring could also be a very soft coil spring, one end acting on the output arm and the other anchored to a point within the casing, the spring axis generally parallel to the axis of the probe filament. The same type of spring could also be arranged to act on a separate arm, similar to the output arm but at a different radial position.

In an alternative embodiment, the device could be integrated with a stepper motor or other actuator connected to handle 30 so that in use the force is applied by the motor rather than manually. Handle 24 would then be supported in a frame or housing to be held level, or at some other desired angle, with the handle 30.

Figure 4:
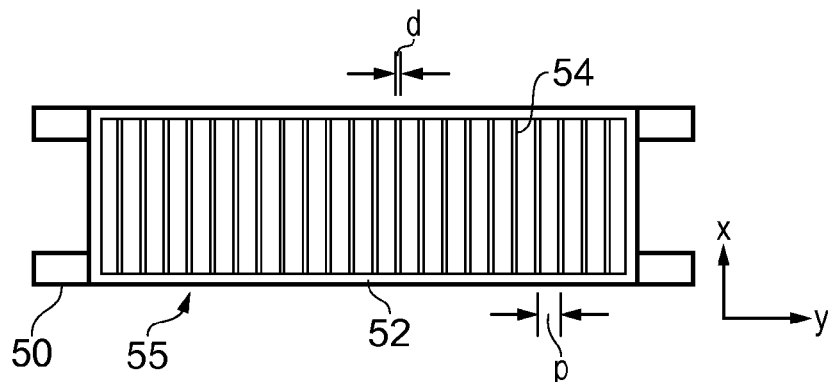
FIG. 4 is a plan view showing the floor of a rodent enclosure.
Figure 5:
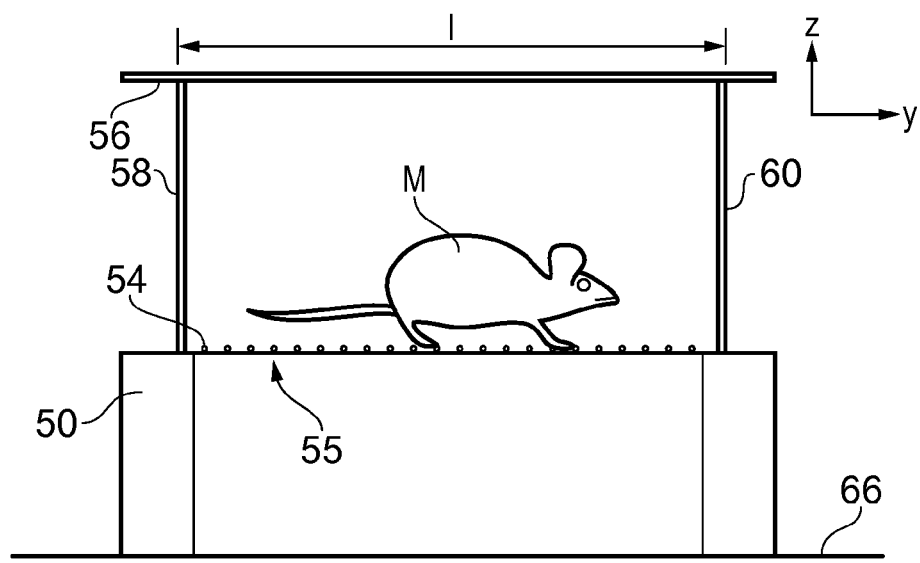
FIG. 5 is a side view of the rodent enclosure of FIG. 4.
Figure 6:
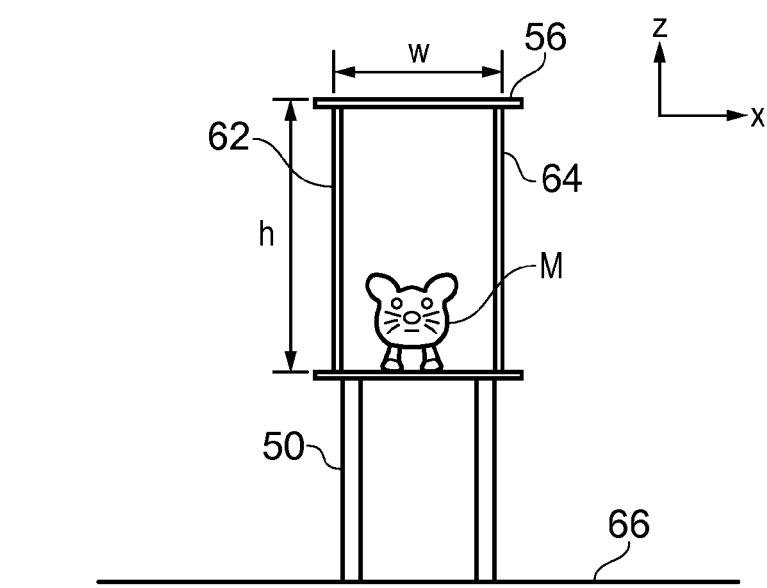
FIG. 6 is an end view of the rodent enclosure of FIGS. 4 and 5.

FIGS. 4, 5 and 6 show a rodent enclosure for a laboratory mouse M.

The enclosure is suitable for use with the force measurement device described with reference to FIGS. 1 to 3, but may also be used with other force measurement devices.

The axes of orientation of the enclosure are shown in FIGS. 4 to 6 and match the axes shown in FIGS. 1 to 3, where the axes correspond to the positioning of the enclosure and measurement device in normal use, with 'z' being vertical.

The enclosure has a length dimension 'l' in the 'y' direction, a breadth or width 'w' in the 'x' direction and a height 'h' in the 'z' direction as illustrated.

The interior of the enclosure is defined by a floor 55, a lid or roof 56, back and front end walls 58 and 60, and left and right side walls 62 and 64 (where the labels left and right are as viewed from the front). At each corner, the enclosure also has support legs 50 which serve to lift the floor of the enclosure above a base surface 66, such as a table top, on which the enclosure is placed. This is to provide a force measurement device as shown in FIGS. 1 to 3 convenient probe filament access through the floor of the enclosure.

The roof, side walls and end walls are preferably see through. For example, they may be made of transparent plastics material, glass, or a mesh or bar structure, or any combination thereof. It will be understood that not all of these panels need to be see through, and some of the panels may have opaque areas as well as transparent areas. The roof is removable to allow a mouse to be placed in and removed from the enclosure. Other design options for introducing and removing the animals are also possible, e.g. via the back and/or front end walls. The end walls, side walls and/or roof may also be made of a transparent, but tinted material. It is well known, for instance, that many strains of mice cannot see through red tinted transparent material and this would, therefore prevent the mouse from seeing the tester while allowing the tester to see the mouse. The measurement arm of the force transducer may also be made of a material of the same color as parts of the rodent enclosure in order to camouflage the measurement arm and probe against the surroundings of the enclosure, so as to make the measurement arm difficult to see for the rodent.

The length, width and height of the enclosure are chosen so that a rodent of pre-specified size, in this case a laboratory mouse is able to move freely on all fours along the length of the enclosure while at the same time being constrained by the side walls of the enclosure to prevent it from turning around while on all fours. The rodent is still able to turn around, but only when standing up on its hind legs. The height of the enclosure is therefore chosen to be high enough to give the rodent freedom to stand up and exhibit natural behavior. Of course a greater height than necessary for standing can be provided.

The floor 55 is constructed of a rectangular frame 52 extending over a horizontal area in 'x' and 'y', with a plurality of bars 54 arranged parallel to each other extending in the 'x' direction and connecting to the frame at each end. The bars have a dimension in the 'y' direction 'd' which if the bars are circular cross-section is a diameter. Alternatively, the bars may be square or rectangular section. In the illustration, the bars have a mutual separation or center-to-center pitch 'p'. In an alternative embodiment, the separation could be varied along the length of the enclosure in a manner such that the rodent is more comfortable to stand in a particular length portion of the enclosure where it is most convenient for an operator to carry out a measurement, typically a central portion away from the ends. The floor bars 54 are illustrated as extending across the full short dimension of the cage to maximize the foot area available. This is desirable, but not essential.

For a mouse, example dimensions are w=3 cm l=15 cm, the floor being constructed of circular bars of diameter 1 mm spaced p=10 mm apart, resulting in a gap between adjacent bars of 9 mm, and height h=10 cm.

For a rat, example dimensions are a width w=7 cm, a length l=35 cm and a height h=20 cm, the floor being constructed of circular bars of diameter 2 mm, on a pitch p=25 mm, resulting in a gap between adjacent bars of 23 mm.

We have established that a rodent, if placed in an enclosure with a floor formed of parallel bars will prefer to have its paws gripping the bars with the toes of the paw rather than resting on the bar with its larger heel area. The bars that form the floor of the enclosure should therefore be of a suitable diameter to be gripped by the toes of the rodent type for which it is designed. Furthermore the spacing of the bars should be slightly greater than the length of the back paw, as measured from the point of the toe to the point of the heel, i.e. front end of toe to back end of heel. A spacing smaller than this will restrict the area of paw available for testing, whereas a spacing significantly larger than this may inhibit natural behavior. Testing is normally carried out on the back paw as it provides the larger plantar area, but, with the present floor arrangement, the front paw may also be used as the rodent will tend also to grip the bars with the toes of the front paw, thereby exposing the plantar or ventral surface of the front paw.

This design maximizes the area of paw available for testing, while still allowing normal and stress-free movement of the paws. Normal behavior is allowed as the animal can move freely along the long axis of the cage and will hence spend the majority of the test time with its paw in the preferred orientation. The width of the run is however sufficient to allow the mouse to stand up on its hind legs and turn around.

With this design of enclosure with a one-dimensional run, the operator finds it relatively straightforward to position a force probe on the mouse's paw.

In use, the operator sits, holding the instrument with the elbows resting on a table of suitable height. The mouse M is placed in the enclosure by removing and replacing the lid 56. For each test, the operator inserts the probe from underneath, locates a paw, and then attempts to apply the force at a fixed rate which should be the same for each test. A proportion of tests will inevitably be invalid because, for instance, the mouse may move away before the threshold is reached or the probe may slip off the paw pad.

Efficient throughput during von Frey testing is aided if the animals are already acclimatized to their surroundings. Additionally, von Frey testing is also often carried out on groups of either four or eight mice (or rats) at one measurement time point. It is therefore an advantage to be able to prepare and then test a group of mice with as little delay as possible between them.

A run assembly can thus be provided which is made up of 2 or more of the cage assemblies previously described, but mounted end-to-end and/or side-by-side in a common framework such that they can all be raised to a convenient height for testing at the same time. This would allow either staggered testing of several mice (first mouse first foot, second mouse first foot, first mouse second foot etc.) or would allow one or more mice to acclimatize to their surroundings while others are being tested.

Such a cage system could contain 2, 3 or 4 sections as described for the individual mouse run with a common lid or, preferably, individual lids. The individual cages may also be detachable from a common framework to facilitate insertion and removal of a mouse from each cage without distracting the other mice.

Figure 7:
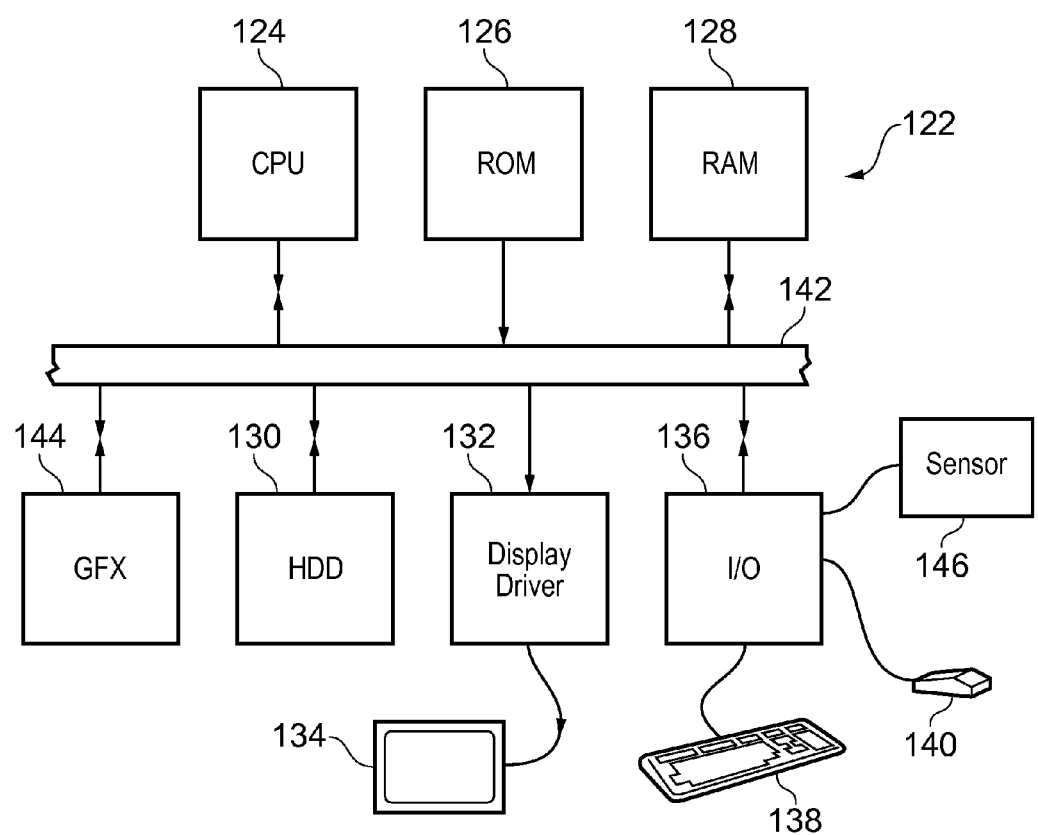
FIG. 7 is a schematic drawing of a data acquisition system including a computer for acquiring and processing force measurement data.

FIG. 7 is a schematic drawing of a data acquisition system including a computer 122 for acquiring and processing force measurement data.

The computer 122 is a general purpose computer configured to perform data acquisition and processing of force measurement data. The computer 122 includes a central processing unit (CPU) 124, a read only memory (ROM) 126, a random access memory (RAM) 128, a mass storage device such as a hard disk drive 130, a display driver 132 and display 134 and a user input/output (IO) circuit 136 with a keyboard 138, force measurement sensor 146 and foot operated switch 140. These devices are connected via a common bus 142. The computer 122 also includes a graphics card 144 connected via the common bus 142. The graphics card includes a graphics processing unit (GPU) and random access memory tightly coupled to the GPU (GPU memory). The CPU 124 may execute program instructions stored within the ROM 126, the RAM 128 or the hard disk drive 130 to carry out processing of acquired data. The RAM 128 and hard disk drive 130 are collectively referred to as the system memory. The GPU may also execute program instructions to carry out processing of data passed to it from the CPU. The force measurement data is received from a sensor 146 of the force measurement device via the I/O 136 or other suitable interface which may be wireless or wired.

The foot operated switch 140 is an example of an operator actuated switch which is provided to allow the operator to label force measurement tests immediately as provisionally valid, i.e. not clearly invalid. A foot operated switch is a convenient option. A finger operated switch is an alternative. Voice commands could also be used. The switch or other command can be set up so that it needs to be actuated within a certain period of time, such as 5 seconds, of the test being completed in order to mark the test as provisionally valid. Alternatively, a specific command could be associated with this approval. The timing of the command can also provide a time stamp to mark against that test which is recorded by the data acquisition computer alongside the force-time record from the transducer. A sound track or audio clip could also be recorded during acquisition so that the operator can add verbal comments which can provide notes to assist subsequent processing, e.g. to assist validation or rejection of measurements.

Figure 8A:
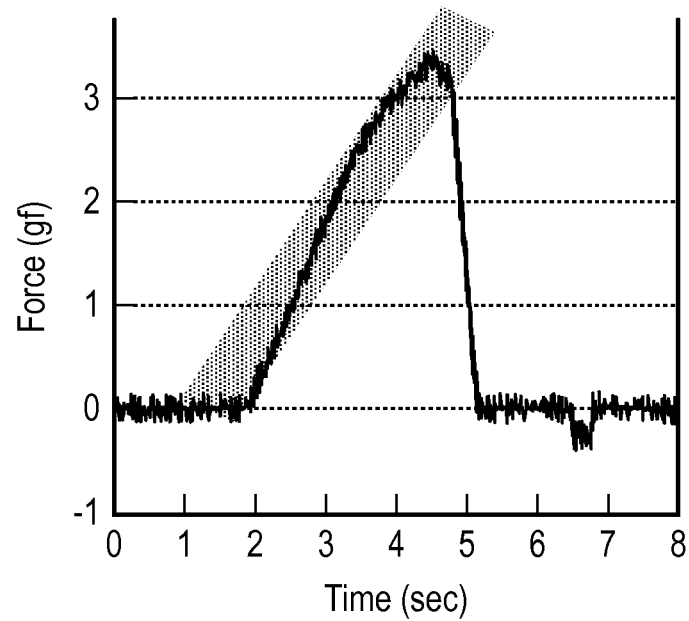
FIG. 8(a) is a graph of force as a function of time for an example valid measurement.

FIG. 8(a) is a graph of force as a function of time for an example valid measurement from a mouse where the predetermined window of force rise rate was set to be between 1 gf/sec to 1.2 gf/sec. In addition (although not indicated on the graph) the condition was set that the maximum force should be maintained for a dwell time of least 0.3 seconds. Smaller or wider windows allowing less or more variation of force rise rate are also possible, including but not limited to 0.5 gf/sec up to 2 gf/sec. When using the visual selection criteria of a rectangular box as shown, which may be moved horizontally across the screen by the user from keyboard or computer mouse controls, the criterion for a valid test is that the entire trace of force rise (neglecting spurious noise as may be present) may be fitted into the selection box. It will be seen that, in the specific example data set of FIG. 8(a), over a period of approximately 3 seconds, the force increases gradually from around zero to 3 gf whereupon a reaction is solicited and the force rapidly drops back to zero as the mouse's paw is withdrawn. It will be seen also that the peak force is maintained for approximately 0.4 seconds, which is considered to be a valid application of force.

Figure 8B:
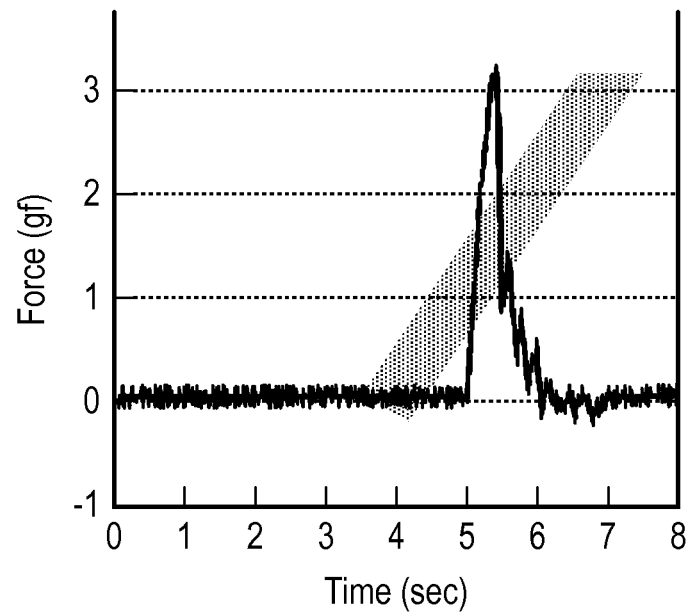
FIG. 8(b) is a graph corresponding to FIG. 8(a) but for invalid measurement.

FIG. 8(b) is a graph corresponding to FIG. 8(a) but showing an invalid force measurement data set. The force has a rise time much less than a second which lies outside the preset window and is far too rapid to represent a valid measurement. It will also be seen that the peak force is only indicated for 0.1 seconds which is considered to be too short for a valid measurement.

Allowing an operator to view the most recently collected data set with a visual overlay of the acceptable tolerances of force rise or ramp rate is also a useful facility in itself, since this can be used by the operator to learn the optimum progression of the force to be applied using the force measurement device.

Figure 9A:
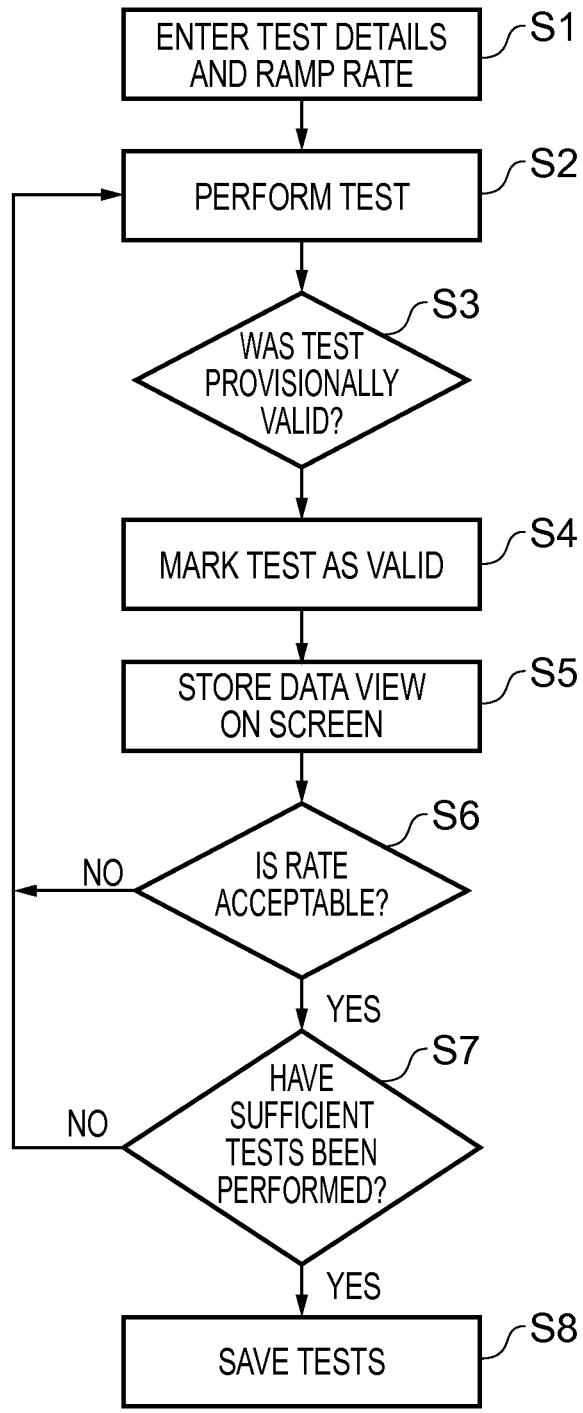
FIG. 9(a) is a flow diagram summarizing the process flow of the protocol used for data acquisition.

FIG. 9(a) is a flow diagram summarizing the process flow of the protocol used for data acquisition.

At box S1, the test criteria such as limits of force rise rate and the dwell time at maximum force are entered into the computer program together with the necessary test identifiers including rodent identifier, study identifiers such as number of tests to be performed, operator etc.

At box S2 the first test is performed.

At box S3 the operator makes their first provisional assessment of whether the test was valid, based on their judgment of the reaction of the rodent. If the answer is no, then the operator is returned to box S2 and performs the next test.

If yes, then the operator, by the operation of a foot or hand switch, or by voice control, marks the test as provisionally valid, at box S4.

At box S5, the computer program the extracts the force ramp from the incoming stream of data and displays it on the computer screen together with an overlaid window of acceptable force rise rate. The operator, at box S6, then compares the force ramp achieved with the required window and, if necessary, prepares to adjust the ramp for the next test.

In the event that the rate was acceptable, the operator then decides, at box S7, whether sufficient tests have been performed and either returns to box S2 to perform another test, or continues to box S8 to save the test data. It will be understood that preferentially the study protocol will permit more tests to be carried out than are eventually required for statistical analysis in the expectation that some will be rejected during the post-test selection process.

Figure 9B:
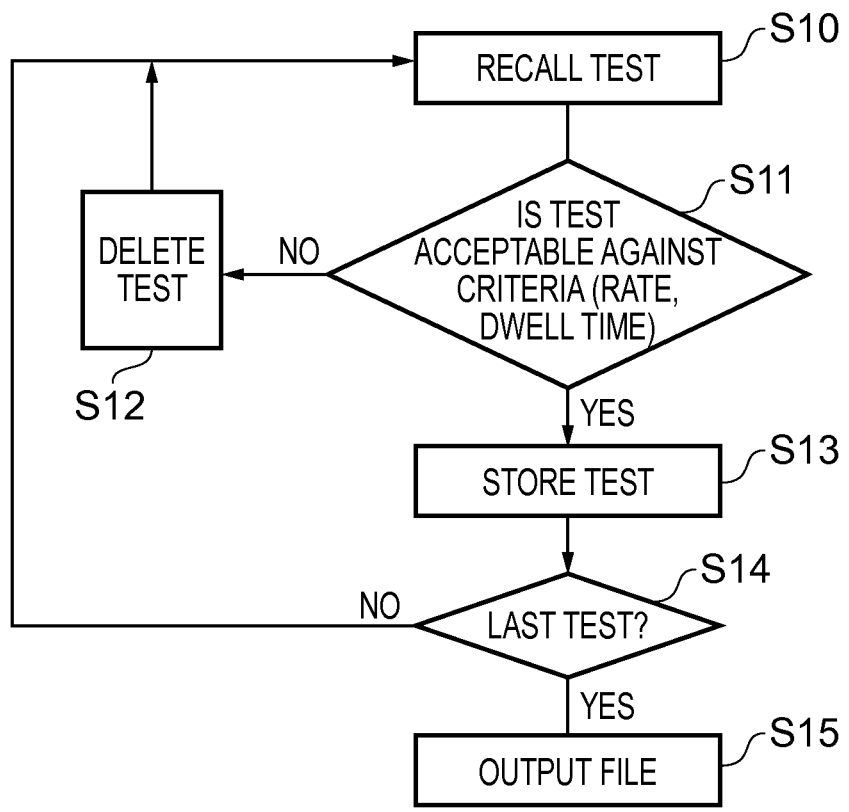
FIG. 9(b) is a flow diagram summarizing the process flow of the protocol used for data processing after acquisition.

FIG. 9(b) is a flow diagram summarizing the process flow of the protocol used for data processing which follows on from the process flow described above for data acquisition.

At box S10 the operator loads the set of tests provisionally marked as valid into the computer program.

At box S11 the operator then compares the test against the preset criteria of force rise rate and dwell time and decides whether to accept and store the test at box 13 or to delete the test at box S12. This process is repeated until the last test is reached whereupon box S14 is passed and the set of finally accepted tests are stored and output at box S15.

The computer program may also include provision for modification of the selection criteria after the completion of the test series if, for example it becomes apparent that the force ramps of all the tests in the data set are very similar to one another, but outside of the original preset window. In this case, the decision may be made that consistency is more important than absolute values and that is it is permissible to change the selection criteria.

Software may be loaded onto the computer from a computer program product bearing the machine executable instructions. The software includes an input part operable to receive sets of force measurement data collected by a force measurement device, each data set being a measurement of force as a function of time.

The software further includes a display part operable to present a graphical user interface to an operator including a graph showing force in known units as a function of time extracted from the force measurement data set. Conveniently, this graphical representation can be presented immediately that the data set is converted and is displayed until superseded by the next valid dataset. The display part includes functionality to optionally overlay each graph with a visual representation of acceptable evolutions of force as a function of time and for the parameters of these acceptable evolutions which may be preset by the operator or otherwise determined from stored data or parameter values.

The software further includes functionality to allow the operator, at the end of an individual test or more likely a test series, to visually assess each graph of force as a function of time, which has been provisionally marked as valid, with respect to the correlation between the actual trace and the overlays of acceptable force time evolutions and other parameters such as the time the peak was held for and the consistency of the rate of increase of force. To effect this, at the conclusion of a test series, software extracts the force-time traces for those tests provisionally indicated by the operator command as being valid and then displays a graph of force against time for each such test. The operator may now compare these graphs with a pre-determined force/time rise rate, superimposed on the test, and discard those which are outside the window. Visual inspection also allows graphs to be discarded where the rate changed during the test, or where the peak force was held for insufficient time for the test to be considered valid.

Based on this assessment, the operator is able to discard any data sets which are not considered to be valid leaving only the valid datasets. Invalid data sets might include, but not be limited to, those where the rate of application of force with time changed significantly during the test, or where the peak force was maintained for insufficient time for the test to be considered valid. The software prompts the operator to input a corresponding decision accepting or rejecting the force measurement data set based on the operator's visual inspection of the graphical user interface.

The software further includes an output part operable to output those force measurement data sets that have been accepted by the operator as valid to be exported for use outside of the software program itself. This includes but is not limited to allowing the data and graphs to be exported to spreadsheet and image file formats. The software may then also measure certain parameters from the force measurement data set, including but not limited to the peak force and the average rate of increase of force with time, and may output these parameters to a spreadsheet.

This approach is fundamentally different to that employed by existing electronic von Frey systems; instead of requiring the operator to necessarily meet all the constraints of the test at the time, our approach is pragmatic, accepting the fact that work with animals is difficult and imprecise, and allowing the operator to intelligently select good data afterwards, but against measurable parameters such as rate of force rise, dwell time at the peak force.

An alternative, simpler, measurement protocol, to which the device could be applied, is to measure, and optionally also record, only peak force for each test. An analog-peak-hold circuit could be used for this purpose which could be manually reset by the user after each test.

While throughout this document we refer to force measurement, it will be understood that pressure is defined as force per unit area, and the relevant area for the tests is defined by the area of the tip which is known and defined. Measurement of pressure for any particular tip is therefore freely convertible to force and vice versa, and therefore encompassed by the present invention.

REFERENCES

[1] Bove: "Mechanical sensory threshold testing using nylon monofilaments: The pain field's "Tin Standard" J Pain, volume 124 (2006) pages 13-17
[2] Millecamps, Laferriére, Ragavendran, Stone, Coderre: "Role of peripheral endothelin receptors in an animal model of complex regional pain syndrome type 1 (CRPS-I)" J Pain, volume 151 (2010) pages 174-183
[3] Ugo Basile Leaflet for Von Frey Hairs (with grid) Cat. No. 37450-277 (2011)
[4] Ugo Basile Leaflet for Dynamic Plantar Aesthesiometer Cat. No. 37450 (2011)
[5] Somedic Technical Specifications—Electronic von Frey 2011

What is claimed is:
1. A force measurement device, comprising:
 a fixed body part and a rotatable body part mutually arranged to allow relative rotation between them about a common rotational axis;
 a resilient biasing member mounted at one end to the fixed body part and at the other end to a rotatable transducer part which is rotatable independently of, and relative to, the rotatable body part;
 a probe having a tip portion extending generally tangentially to the rotational axis and terminating at one end in a tip and at the other end in a junction with an end of an arm portion, the arm portion extending generally radially to the rotational axis and connecting at another end to the rotatable transducer part so that angular displacement of the fixed part relative to the arm portion stores or releases energy in the resilient biasing member and also causes rotation of the transducer part relative to the fixed body part; and
 a rotation sensor operable to detect the amount of angular displacement between the transducer part and the fixed body part, and to output a measurement parameter having values that are calibrated against force values associated with forces applied to the probe's tip.

2. The device of claim 1, wherein the fixed body part and the rotatable body part each have a handle portion to allow the device to be held in each hand by an operator.

3. The device of claim 1, wherein the rotatable transducer part comprises a rotatable sensor element which is arranged facing a fixed sensor element attached to the fixed body part, wherein relative rotation of the rotatable and fixed sensor elements causes variation in the value of the measurement parameter.

4. The device of claim 3, wherein the rotatable and fixed sensor elements are plates with electrically conductive portions patterned so that an area of mutual overlap between the plates, as viewed in the direction of their common rotational axis, varies with an amount of relative rotation of the rotatable and fixed sensor elements, the measurement parameter being capacitance between the plates.

5. The device of claim 4, wherein the area of mutual overlap when no energy is stored in the resilient biasing element is at least 10% of a maximum mutual overlap.

6. A kit comprising:
a force measurement device according to claim 1; and
a rodent enclosure dimensioned in length, width and height so as to form a run for a rodent of pre-specified size and type along the length of the enclosure between its ends,
wherein the width is dimensioned to allow the rodent to run freely along the length of the enclosure,
wherein the width is limited, at least away from the ends of the enclosure, so that the rodent cannot turn around while standing on all fours, but can turn around when standing on its hind legs, and
wherein the enclosure has a floor with apertures along its length and width to allow access for the probe from below to the rodent's paw pads.

7. The kit of claim 6 further comprising:
a nontransitory, tangible computer program product bearing machine executable instructions operable to:
(a) receive sets of force measurement data collected by the force measurement device, each data set being a measurement of force as a function of time;
(b) present a graphical user interface to an operator including, for each force measurement date set, (i) a graph showing force as a function of time extracted from the force measurement data set (ii) a visual representation of a range of acceptable evolutions of force as a function of time overlaid on the graph, and (iii) an input via which the operator is prompted to provide an input decision accepting or rejecting the force measurement data set based on the operator's visual inspection of the graphical user interface; and
(c) output those force measurement data sets that have been accepted by the operator as validated force measurement data sets.

8. A kit comprising:
an assembly of parts for assembling the force measurement device according to claim 1; and
a rodent enclosure dimensioned in length, width and height so as to form a run for a rodent of pre-specified size and type along the length of the enclosure between its ends,
wherein the width is dimensioned to allow the rodent to run freely along the length of the enclosure,
wherein the width is limited, at least away from the ends of the enclosure, so that the rodent cannot turn around while standing on all fours, but can turn around when standing on its hind legs, and
wherein the enclosure has a floor with apertures along its length and width to allow access for a force sensor's probe filament from below to the rodent's paw pads or an assembly of parts therefor.

9. The kit of claim 8 further comprising:
a nontransitory, tangible computer program product bearing machine executable instructions operable to:
(a) receive sets of force measurement data collected by the force measurement device when assembled, each data set being a measurement of force as a function of time;
(b) present a graphical user interface to an operator including, for each force measurement data set, (i) a graph showing force as a function of time extracted from the force measurement data set (ii) a visual representation of a range of acceptable evolutions of force as a function of time overlaid on the graph, and (iii) an input via which the operator is prompted to provide an input decision accepting or rejecting the force measurement data set based on the operator's visual inspection of the graphical user interface; and
(c) output those force measurement data sets that have been accepted by the operator as validated force measurement data sets.

* * * * *